US00PP33016P2

(12) United States Plant Patent
van Geest

(10) Patent No.: US PP33,016 P2
(45) Date of Patent: May 4, 2021

(54) ***MANDEVILLA* PLANT NAMED 'ESDEFL1'**

(50) Latin Name: ***Mandevilla sanderi* (Hemsl.) Woodson**
Varietal Denomination: ESDEFL1

(71) Applicant: J. Van Geest Holding B.V., Gravenzande (NL)

(72) Inventor: Jan van Geest, Gravenzande (NL)

(73) Assignee: J. Van Geest Holding B.V., Gravenzande (NL)

( * ) Notice: Subject to any disclaimer, the term of this patent is extended or adjusted under 35 U.S.C. 154(b) by 0 days.

(21) Appl. No.: 16/873,492

(22) Filed: Apr. 21, 2020

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 6/088
See application file for complete search history.

(56) References Cited

PUBLICATIONS

UPOV hit on a *Mandevilla* plant named, 'ESDEFL1', QZ PBR 49726, granted Jun. 19, 2018 and published Aug. 16, 2016.*

* cited by examiner

*Primary Examiner* — Anne Marie Grunberg
(74) *Attorney, Agent, or Firm* — Samuel R. McCoy, Jr.

(57) ABSTRACT

A new and distinct *Mandevilla* plant named 'ESDEFL1' which is characterized by a compact growth habit, dark green and glossy foliage, medium-sized dark red flowers with a darker red throat and yellow-orange floral tube, as well as the stability of these characteristics from generation to generation.

3 Drawing Sheets

Latin name of the genus and species: The Latin name of the genus and species of the novel variety disclosed herein is *Mandevilla sanderi* (Hemsl.) Woodson.

Variety denomination: The inventive variety of *Mandevilla* disclosed herein has been given the variety denomination 'ESDEFL1'.

BACKGROUND OF THE INVENTION

Parentage: 'ESDEFL1' is a seedling selection from bulked seed that was produced from the open pollination of a plurality of cultivated, phenotypically-similar unnamed *Mandevilla sanderi* plants (not patented). In October of 2014, seed harvested from said *Mandevilla sanderi* plants was sown at a commercial greenhouse in Gavenzande, the Netherlands and allowed to grow to maturity for observation. In the summer of 2015, one plant from this bulked *Mandevilla sanderi* seed was observed to exhibit unique growth and flower characteristics and was isolated for further evaluation in order to confirm the distinctness and stability of the characteristics first observed. Upon confirmation of distinctness and stability, 'ESDEFL1' was selected for commercialization.

Asexual Reproduction: Asexual reproduction of the new cultivar 'ESDEFL1', by way of softwood stem cuttings, was first initiated in the summer of 2015 at a commercial greenhouse in Gavenzande, The Netherlands. Through four subsequent generations, the unique features of this cultivar have proven to be stable and true to type.

SUMMARY OF THE INVENTION

The cultivar 'ESDEFL1' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ESDEFL1'. These characteristics in combination distinguish 'ESDEFL1' as a new and distinct *Mandevilla* cultivar:

1. *Mandevilla* 'ESDEFL1' exhibits a compact growth habit; and
2. *Mandevilla* 'ESDEFL1' exhibits smooth, dark green and glossy foliage; and
3. *Mandevilla* 'ESDEFL1' exhibits a medium-sized dark red flower petals with a darker red floral throat and yellow-orange inner corolla tube.

BOTANICAL DESCRIPTION OF THE PLANT

Figure 1:
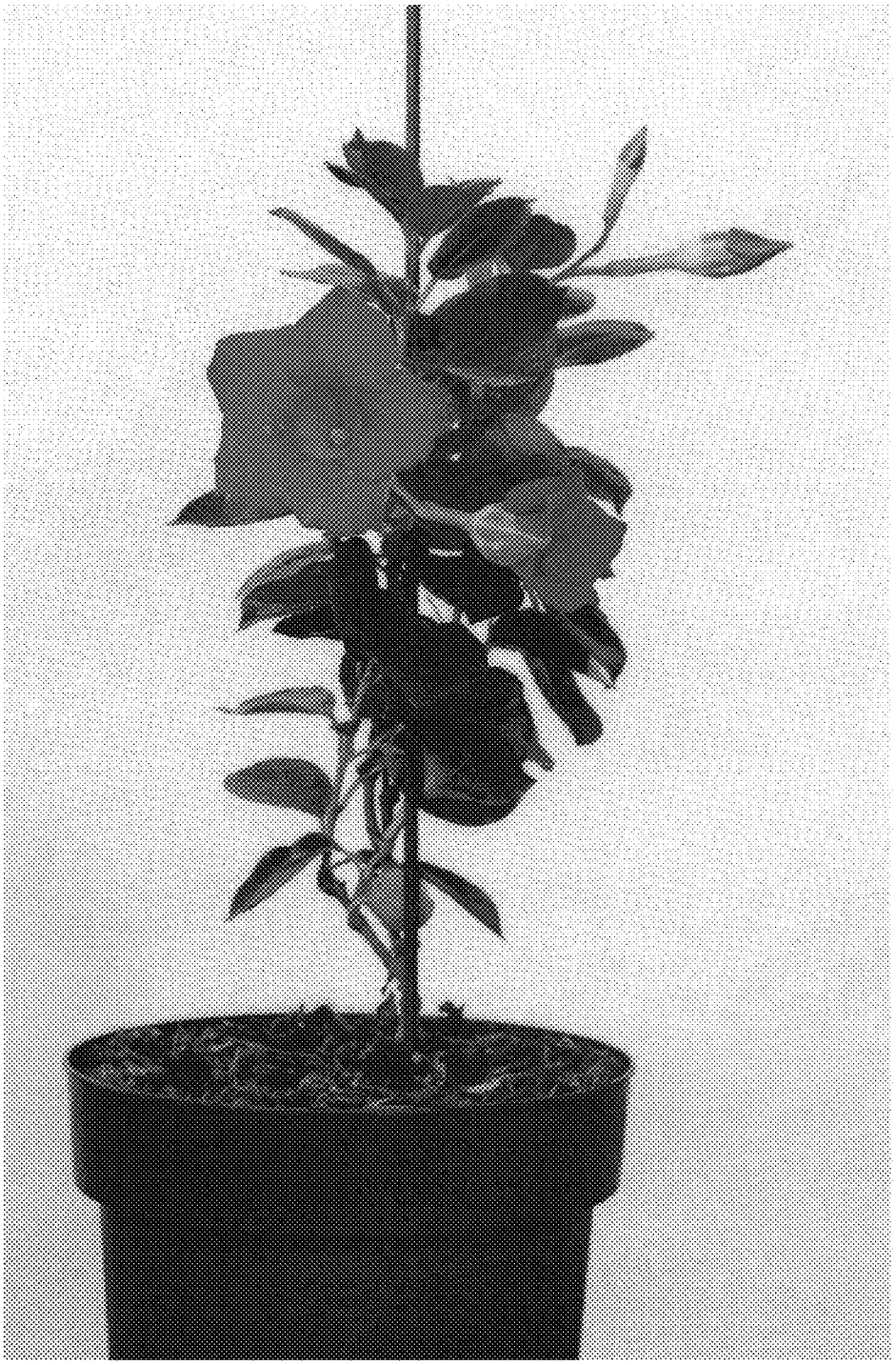
FIG. 1. illustrates, as nearly true as it is reasonably possible to make the same in color photographs of this type, an exemplary plant of 'ESDEFL1' in flower, grown in a commercial greenhouse in Gavenzande, the Netherlands.
Figure 2:
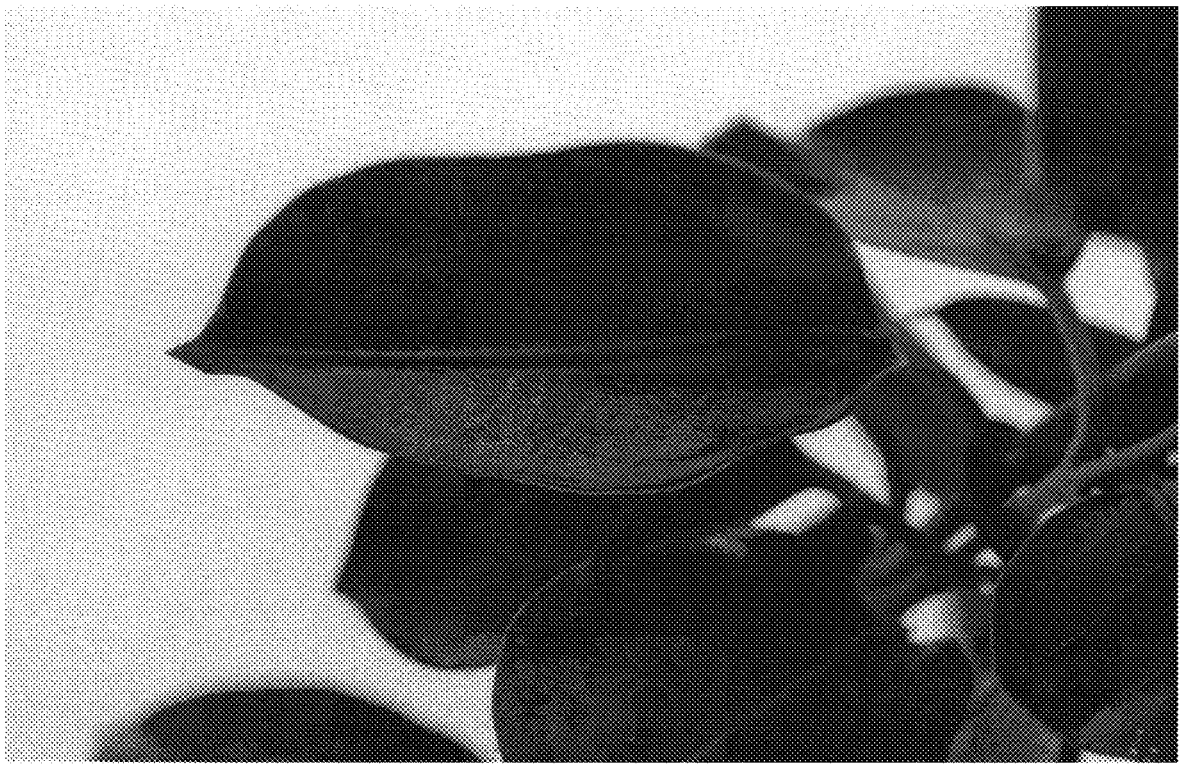
FIG. 2. illustrates, as nearly true as it is reasonably possible to make the same in color photographs of this type, the foliage of 'ESDEFL1'.
Figure 3:
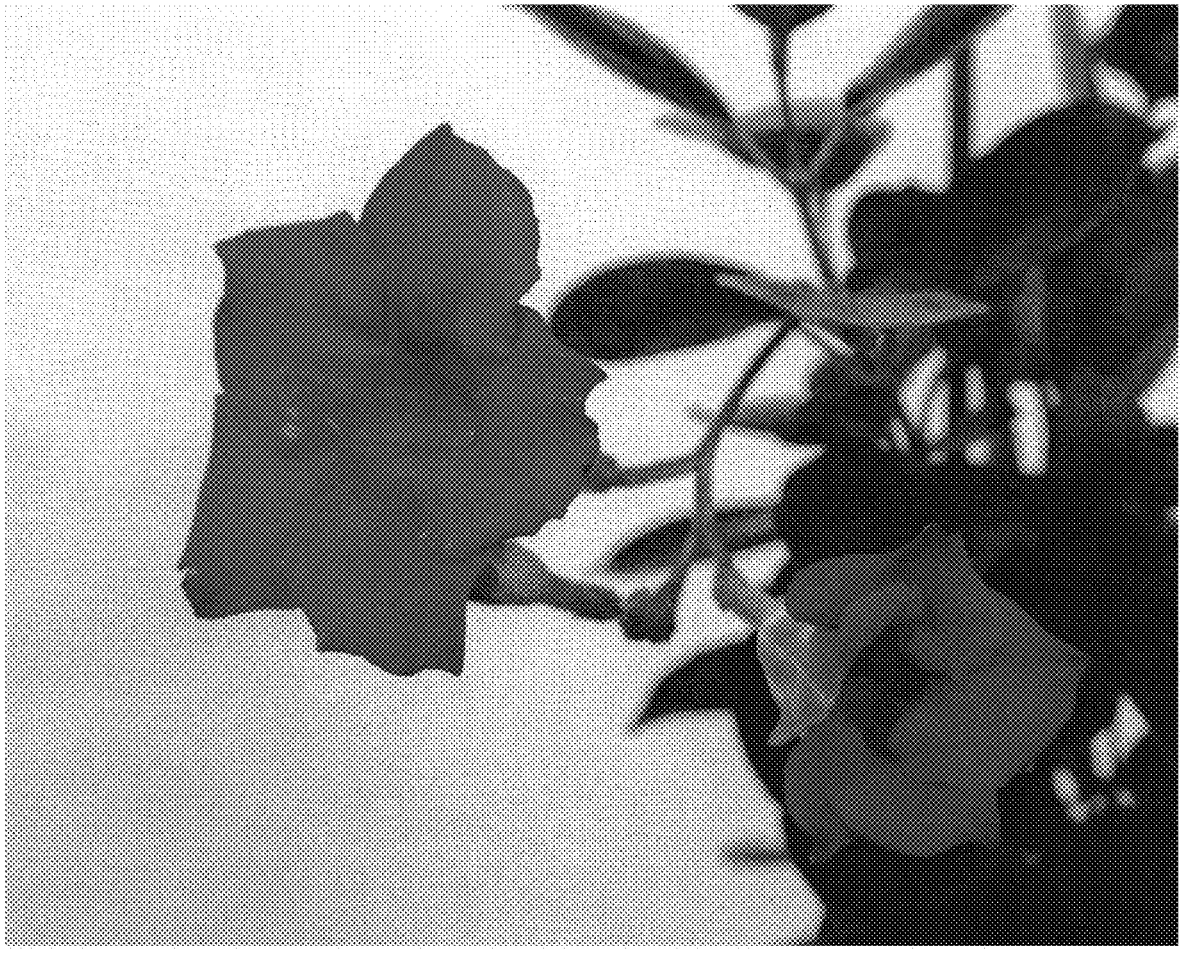
FIG. 3. illustrates, as nearly true as it is reasonably possible to make the same in color photographs of this type, the flower of 'ESDEFL1'.

The following observations and measurements were made in October of 2019 and describe averages from a sample set of six specimens of 12 month old 'ESDEFL1' plants grown in 19 cm nursery pots grown in a greenhouse in Gavenzande, The Netherlands. Plants were grown in full sun exposure and regularly watered with overhead irrigation. No pest or disease measures were taken.

Those skilled in the art will appreciate that certain characteristics will vary with older or, conversely, with younger plants. 'ESDEFL1' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 (sixth edition).

A botanical description of 'ESDEFL1' and comparisons with the presumed parent and most similar known variety of *Mandevilla sanderi* are provided below.

Plant description:

*Growth habit*.—Vining perennial; broad upright.

*Plant shape*.—Obovate to broad obovate.

*Average height from base to top of foliage*.—34.6 cm.

*Average height from base to top of the floral plane*.—29.0 cm.

*Average width*.—35.3 cm.

*Growth rate*.—Moderately fast growing.

*Plant vigor*.—Moderately vigorous.

*Propagation*.—Type — Softwood stem cuttings. Time to initiate rooting — Approximately 42 days at 21 degrees Celsius. Time to Produce a Finished Plant — Approximately 9 months are required to produce a fully rooted and marketable plant in a 19 cm nursery container.

*Disease and pest resistance or susceptibility*.—Plants have not been observed to be susceptible or resistant to pathogens and pests common to *Mandevilla sanderi*.

*Environmental tolerances*.—Adapt to at least USDA Zones 10 and 12, and temperatures ranging from at least 5 degrees to 40 degrees Celsius; moderate tolerance to rain; low to moderate tolerance to wind; moderate tolerance to drought.

Root system:

*General*.—Freely branching; moderately dense rooting.

*Texture*.—Fibrous.

*Color*.—Light brown.

Stem:

*Branching habit*.—Basally branching main stem; freely branching with lateral branches.

*Number of main stems per plant*.—2.

*Number of lateral branches per plant*.—5.

*Appearance; cross-section*.—Rounded.

*Length of lateral branches*.—15.9 cm.

*Diameter of lateral branches*.—0.3 cm at the widest point.

*Internode length on lateral branches*.—3.2 cm

*Aspect*.—Upright; angle is approximately 35 degrees from vertical plane.

*Strength*.—Strong.

*Color, juvenile*.—Yellow-green, in between RHS 144B.

*Color, mature*.—Yellow-green, in between RHS 144B.

*Color at internodes*.—Yellow-green, in between RHS 144B.

*Texture and luster*.—Glabrescent and moderately glossy.

*Color of bark on main stems*.—Brown, nearest to RHS 200D.

*Other stem characteristics*.—Stems produce a milky sap when damaged.

Foliage:

*Arrangement*.—Opposite.

*Division*.—Simple.

*Quantity*.—Approximately 10 leaves per stem, as observed.

*Lamina*.—Dimensions — 6.2 cm long and 4.8 cm wide, on average. Shape — Broad obovate to broad elliptic. Aspect — Concave; slightly reflexed. Apex — Abruptly acute. Base — Rounded. Margin — Entire; not undulated. Pubescence, texture and luster of adaxial surface — Glabrous, smooth, and moderately glossy. Pubescence, texture and luster of abaxial surface — Glabrous, smooth, and slightly to moderately glossy. Color — Juvenile foliage, adaxial surface — Nearest to in between green and yellow-green, RHS 139A and 147A. Juvenile foliage, abaxial surface — Grey-brown, nearest to in between RHS N199A and N199B. Mature foliage, adaxial surface — Nearest to in between yellow-green and greyed-green, RHS 147A and N189A. Mature foliage, abaxial surface — Yellow-green, nearest to RHS 146B. Venation — Pattern — Pinnate. Venation color, adaxial surface — Yellow-green, nearest to RHS 144A. Venation color, abaxial surface — Yellow-green, nearest to RHS 145B.

*Petiole*.—Length — 1.8 cm. Width — 0.2 cm. Texture — Smooth and glabrous. Luster — Moderately glossy. Strength — Moderately strong. Color, adaxial surface — Yellow-green, nearest to in between RHS 146B and 146C. Color, abaxial surface — Yellow-green, nearest to RHS 144B.

Inflorescence:

*Inflorescence arrangement*.—Axillary racemes.

*Dimensions*.—12.9 cm high, including the peduncle, and 14.4 cm in diameter.

*Natural flowering season*.—Spring through autumn in USDA Hardiness Zones 10 through 12.

*Time to flower*.—Approximately 10 weeks from planting a rooted cutting.

*Quantity of flowers per inflorescence*.—3 on average; varying from 2 to 4.

*Quantity of flowers per plant*.—2.

*Quantity of flower buds per plant*.—5.

*Quantity of flowers and flower buds per plant*.—7.

*Peduncle*.—Dimensions — 6.3 cm long and 0.25 cm in diameter. Aspect — Upward and outward; at approximately 35 degrees to the lateral branch axis. Strength — Moderately strong. Texture and luster — Glabrous and moderately glossy. Color — Yellow-green, nearest to RHS 144A.

Bud:

*Shape*.—Oblanceolate.

*Dimensions*.—5.1 cm long and 1.2 cm in diameter.

*Pubescence, texture and luster*.—Glabrous, smooth and slightly glossy.

*Color*.—The distal portion of the bud is red, nearest to RHS 46A; the middle section is yellow-green, nearest to RHS 145B; the proximal portion of the bud is yellow-green, nearest to RHS 145A.

Flower:

*Flowering habit*.—Moderately free flowering.

*Shape*.—Funnelform.

*Total length*.—6.5 cm.

*Total diameter*.—8.4 cm.

*Floral throat diameter*.—2.5 cm.

*Attitude*.—Flowers are outward facing.

*Fragrance*.—Non-fragrant.

*Lastingness*.—Approximately 10 days.

*Persistent*.—Self-cleaning.

*Pedicels*.—Dimensions — 1.8 cm long and 0.3 cm in diameter. Aspect — Upward and outward; approximately 20 degrees to the peduncle axis. Strength — Moderately strong. Texture and luster — Glabrous, smooth, and moderately glossy. Color — Yellow-green, nearest to RHS 144B.

*Petals*.—Quantity of Petals — 5. Arrangement — Single whorl; petals imbricate and fused into an elongated tube at the base; lower 60 percent of the petals are fused. Shape of petal lobes — Spatulate. Length — 8.8 cm. Width — 3.8 cm at the base of the free portion of the petal. Apex — Unequally, bluntly apiculate. Base — Fused at the base. Margin — Entire; moderately to highly undulated. Aspect — Moderately reflexed. Pubescence, texture and luster of upper surface — Glabrous, velvety and very slightly glossy. Pubescence, texture and luster of lower surface — Glabrous, moderately velvety and slightly glossy. Petal lobe color when opening, upper surface — Red, nearest to RHS N45A; floral throat is red, nearest to RHS 46A. No visible venation. Petal lobe color when opening, lower surface — Red, nearest to in between RHS 53A and 53B, and fading lighter towards the floral tube, nearest to RHS 54A. Main vein is white, nearest to RHS N155B; no other venation is visible. Petal lobe color when fully opened, upper surface — Red, nearest to RHS N45B. The floral throat is red, nearest to in between RHS N45A and 46A. No visible venation. Petal color does not fade with age. Petal lobe color when fully opened, lower surface — Red, nearest to RHS 53C, and fading lighter towards the floral tube, nearest to RHS 54A. Main vein is red-purple, nearest to RHS 73D; no other venation is visible. Petal color does not fade with age.

*Floral tube*.—Diameter of floral tube — 0.7 cm, on average, along the entire length of the floral tube. Distal most portion of the tube is 2.5 cm at the widest point. Length of floral tube — 5.3 cm. Texture — Smooth; glabrous. Inner floral tube color, when fully opened — Outer portion is orange-red, nearest to RHS 31A, suffused with red-purple, nearest to RHS 58B; narrow portion of the tube is yellow-green, RHS 145A. No venation is visible. Outer floral tube color, when fully opened — Red-purple, nearest to RHS 58B, and fading to yellow-green towards the narrow portion of the tube, nearest to in between RHS 145C and 145D; narrow portion of the floral tube is yellow-green, nearest to RHS 144B. No visible venation.

*Calyx*.—Calyx dimensions — 1.0 cm in diameter and 0.7 cm in diameter. Arrangement — Sepals are free, rotate. Sepals — Quantity — 5. Shape — Narrow triangular to lanceolate. Sepal dimensions — 0.9 cm long and 0.3 cm wide at the base. Apex — Narrow acuminate. Base — Cuneate. Margin — Entire; not undulated. Pubescence, texture and luster, upper surface — Smooth; glabrous; slightly glossy. Pubescence, texture and luster, lower surface — Smooth; glabrous; very slightly glossy. Color when opening, upper surface — Yellow-green, nearest to in between RHS 144A and 144B; margined red, nearest to RHS 38D; tipped red, nearest to RHS 42B. Color when opening, lower surface — Yellow-green, nearest to in between RHS 144A and 144B; margined red, nearest to RHS 37C; tipped red, nearest to in between RHS 42A and 42B. Color when fully opened, upper surface — Yellow-green, nearest to in between RHS 144A and 144B; margined red, nearest to RHS 38D; tipped red, nearest to RHS 42B. Color when fully opened, lower surface — Yellow-green, nearest to in between RHS 144A and 144B; margined red, nearest to RHS 37C; tipped red, nearest to in between RHS 42A and 42B.

Reproductive organs:

*Androecium*.—Stamen quantity — 5. Filament attachment — Adnate. Filament length — 0.3 cm. Filament color — Yellow-green, nearest to in between RHS 151B and 151C. Filament texture — Densely covered with short hairs of approximately 1.0 mm long; hairs are colored white, RHS 155D. Anther attachment — Basifixed. Anther shape — Narrowly sagitate with tips touching and thus forming a small, narrow cone. Anther length — 1.0 cm. Anther width — 0.175 cm. Anther color — Greyed-yellow, nearest to RHS 162C. Anther aspect — The five anthers are touching at their apices, thus forming a cone of anthers. Pollen, presence — None detected.

*Gynoecium*.—Pistil quantity — 1. Pistil length — 3.0 cm. Style length — 2.7 cm. Style color — Yellow-green, nearest to RHS 145D. Stigma shape — Club-shaped. Stigma length — 0.3 cm. Stigma diameter — 0.3 cm. Stigma color — Yellow-green, nearest to RHS 147D. Ovary color — Yellow-green, nearest to in between RHS 144B and 144C.

Seed and fruit: None observed.

COMPARISONS WITH THE PARENT PLANTS

Plants of the new cultivar 'ESDEFL1' differ from the phenotypically-similar population of unnamed *Mandevilla sanderi* plants from which seed was bulked by the characteristics described in Table 1. Although the exact parentage is unknown, it is probable that both the seed parent and pollen parent originated from within the population as it was geographically isolated from any other *Mandevilla sanderi* plants.

TABLE 1

| Characteristic | 'ESDEFL1' | Phenotypically-similar, unnamed *Mandevilla sanderi* plants |
|---|---|---|
| General coloration of the foliage. | Lighter shade of green. | Darker shade of green. |
| Flower size. | Larger than the parent | Smaller than 'ESDEFL'. |
| General coloration of the flower. | Darker shade of red. | Lighter shade of red. |

COMPARISON WITH THE MOST SIMILAR *MANDEVILLA* CULTIVAR KNOWN TO THE INVENTOR

Plants of the new cultivar 'ESDEFL1' may be distinguished from the most similar known commercial comparator, *Mandevilla* 'Rio Deep Red' (not patented) by the characteristics described in Table 2.

TABLE 2

| Characteristic | 'ESDEFL1' | 'Rio Deep Red' |
|---|---|---|
| Foliage luster. | Glossier than 'Rio Deep Red'. | Less glossy than 'ESDEFL1'. |
| Growth habit. | More compact than 'Rio Deep Red'. | Less compact than 'ESDEFL1'. |
| Flower color when fully opened. | Darker red than 'Rio Deep Red'. | Lighter shade of red compared to 'ESDEFL1'. |

That which is claimed is:

1. A new and distinct variety of *Mandevilla* plant named 'ESDEFL1', substantially as described and illustrated herein.

* * * * *